US009410912B2

(12) United States Patent
Yamada et al.

(10) Patent No.: US 9,410,912 B2
(45) Date of Patent: Aug. 9, 2016

(54) BIOLOGICAL GAS DETECTION APPARATUS AND BIOLOGICAL GAS DETECTION METHOD

(75) Inventors: Yuuki Yamada, Chiyoda-ku (JP); Satoshi Hiyama, Chiyoda-ku (JP); Yuki Moritani, Chiyoda-ku (JP); Mariko Sugimura, Itami (JP); Kazuo Onaga, Itami (JP); Katsuyuki Tanaka, Itami (JP)

(73) Assignees: NTT DOCOMO, INC., Tokyo (JP); FIS Inc., Itami-shi (JP)

( * ) Notice: Subject to any disclaimer, the term of this patent is extended or adjusted under 35 U.S.C. 154(b) by 357 days.

(21) Appl. No.: 13/978,576

(22) PCT Filed: May 18, 2012

(86) PCT No.: PCT/JP2012/062876
§ 371 (c)(1),
(2), (4) Date: Jul. 8, 2013

(87) PCT Pub. No.: WO2012/165182
PCT Pub. Date: Dec. 6, 2012

(65) Prior Publication Data
US 2013/0283889 A1 Oct. 31, 2013

(30) Foreign Application Priority Data
May 27, 2011 (JP) ................................. 2011-119513

(51) Int. Cl.
*G01N 27/12* (2006.01)
*G01N 33/00* (2006.01)
*G01N 33/497* (2006.01)

(52) U.S. Cl.
CPC ............ *G01N 27/12* (2013.01); *G01N 33/0031* (2013.01); *G01N 33/497* (2013.01)

(58) Field of Classification Search
CPC ........................................................ G01N 27/12
USPC .............. 73/23.3, 23.24, 31.06; 340/632, 634
See application file for complete search history.

(56) References Cited

U.S. PATENT DOCUMENTS 4,542,640 A * 9/1985 Clifford ........................ 73/31.06
4,586,143 A   4/1986 Kaneyasu et al.
(Continued)

FOREIGN PATENT DOCUMENTS

JP    58-162851 A    9/1983
JP    2-198350 A    8/1990
(Continued)

OTHER PUBLICATIONS

Partial Supplementary European Search Report issued on Nov. 11, 2014, in Patent Application No. 12792138.5.
(Continued)

*Primary Examiner* — Hezron E Williams
*Assistant Examiner* — Hoang Nguyen
(74) *Attorney, Agent, or Firm* — Oblon, McClelland, Maier & Neustadt, L.L.P.

(57) ABSTRACT

A biological gas detection apparatus of an embodiment of the present invention includes: a sensor unit including plural types of gas sensors; a control unit of the sensor unit; a data recording unit; and a data analyzing unit, wherein the data recording unit includes a database on properties of sensitivities of the gas sensors for a single body of a desired gas component, a single body of an interference gas component, and a mixed gas of these that are included in the biological gas, and the data analyzing unit calculates concentration of the desired gas component based on sensitivities of the gas sensors output when detecting the biological gas and the database.

13 Claims, 14 Drawing Sheets

(56) References Cited

U.S. PATENT DOCUMENTS

| | | | | |
|---|---|---|---|---|
| 4,638,443 | A | * | 1/1987 | Kaneyasu et al. ............... 702/24 |
| 4,911,892 | A | * | 3/1990 | Grace et al. .................... 422/94 |
| 5,417,821 | A | * | 5/1995 | Pyke ............................. 205/775 |

FOREIGN PATENT DOCUMENTS

| | | |
|---|---|---|
| JP | 5 203598 | 8/1993 |
| JP | 7 270360 | 10/1995 |
| JP | 9 504613 | 5/1997 |
| JP | 2001 349888 | 12/2001 |
| JP | 2002 31615 | 1/2002 |
| JP | 2002-62276 A | 2/2002 |
| JP | 2006 75447 | 3/2006 |
| JP | 2009 257772 | 11/2009 |
| JP | 2010-22554 A | 2/2010 |
| JP | 2010-25716 A | 2/2010 |
| JP | 2010-25718 A | 2/2010 |
| JP | 2010 26746 | 2/2010 |
| JP | 2010-249556 A | 11/2010 |

OTHER PUBLICATIONS

Extended European Search Report issued Feb. 6, 2015 in Patent Application No. 12792138.5.
International Search Report Issued Jul. 3, 21012 in PCT/JP11/062876 Filed May 18, 2012.
Office Action issued Aug. 5, 2014 in Japanese Patent Application No. 2013-517966 (with English language translation).
Combined Chinese Office Action and Search Report issued Nov. 27, 2014 in Patent Application No. 201280019930.0 (with English language translation).
Office Action issued Jul. 30, 2015 in Chinese Patent Application No. 201280019930.0 (with English language translation).

\* cited by examiner

FIG.6

| | NUMBER | GAS CONCENTRATION [ppm] | | | SENSITIVITY | | GAS SENSOR A SENSITIVITY/ GAS SENSOR B SENSITIVITY | SUM OF GAS SENSOR A SENSITIVITY AND GAS SENSOR B SENSITIVITY |
|---|---|---|---|---|---|---|---|---|
| | | ACETONE | ETHANOL | HYDROGEN | GAS SENSOR A | GAS SENSOR B | | |
| ACETONE CONCENTRATION DIFFERENCE | [1] | 0.5 | 0 | 10 | 0.673 | 0.753 | 0.893 | 1.427 |
| | [2] | 5 | 0 | 10 | 0.133 | 0.600 | 0.222 | 0.733 |
| | [3] | 10 | 0 | 10 | 0.090 | 0.532 | 0.170 | 0.622 |
| ETHANOL CONCENTRATION DIFFERENCE | [4] | 1 | 10 | 10 | 0.251 | 0.453 | 0.554 | 0.704 |
| | [5] | 1 | 30 | 10 | 0.175 | 0.352 | 0.497 | 0.527 |
| | [6] | 1 | 100 | 10 | 0.104 | 0.256 | 0.407 | 0.360 |
| HYDROGEN CONCENTRATION DIFFERENCE | [7] | 1 | 0 | 30 | 0.396 | 0.417 | 0.948 | 0.813 |
| | [8] | 1 | 0.1 | 100 | 0.344 | 0.287 | 1.198 | 0.632 |
| HIGH CONCENTRATION MIXTURE GAS | [9] | 10 | 30 | 10 | 0.082 | 0.335 | 0.246 | 0.417 |
| | [10] | 10 | 100 | 10 | 0.069 | 0.245 | 0.281 | 0.314 |
| | [11] | 10 | 100 | 100 | 0.069 | 0.208 | 0.334 | 0.277 |

FIG.11

| | | NUMBER | MEASUREMENT RESULT BY GAS CHROMATOGRAPHY [ppm] | | | SENSOR SENSITIVITY | | GAS SENSOR A SENSITIVITY / GAS SENSOR B SENSITIVITY | SUM OF GAS SENSOR A SENSITIVITY AND GAS SENSOR B SENSITIVITY |
|---|---|---|---|---|---|---|---|---|---|
| | | | ACETONE | ETHANOL | HYDROGEN | GAS SENSOR A | GAS SENSOR B | | |
| NO DRINKING | TEST SUBJECT 1 | [1] | 0.152 | 0 | 27.7 | 0.375 | 0.347 | 1.081 | 0.722 |
| | TEST SUBJECT 2 | [2] | 0.834 | 0 | 16.1 | 0.402 | 0.374 | 1.075 | 0.776 |
| | TEST SUBJECT 3 | [3] | 0.7 | 0 | 13.5 | 0.44 | 0.388 | 1.133 | 0.828 |
| | TEST SUBJECT 4 | [4] | 0.034 | 0 | 5.7 | 0.571 | 0.387 | 1.476 | 0.958 |
| | TEST SUBJECT 5 | [5] | 0.607 | 0 | 59.5 | 0.328 | 0.29 | 1.131 | 0.618 |
| | TEST SUBJECT 6 | [6] | 0.151 | 0 | 0.5 | 0.417 | 0.502 | 0.831 | 0.919 |
| | TEST SUBJECT 7 | [7] | 0.304 | 0 | 25 | 0.459 | 0.423 | 1.085 | 0.882 |
| DRINKING EXPERIMENT | 5 MINUTES AFTER DRINKING | [8] | 0.517 | 80 | 11 | 0.088 | 0.243 | 0.363 | 0.331 |
| | 15 MINUTES AFTER DRINKING | [9] | 0.807 | 18.9 | 15.7 | 0.152 | 0.288 | 0.529 | 0.44 |
| | 30 MINUTES AFTER DRINKING | [10] | 0.843 | 11.1 | 15.5 | 0.18 | 0.323 | 0.557 | 0.503 |
| | 60 MINUTES AFTER DRINKING | [11] | 0.927 | 0.3 | 18 | 0.315 | 0.3 | 1.049 | 0.615 |

BIOLOGICAL GAS DETECTION APPARATUS AND BIOLOGICAL GAS DETECTION METHOD

TECHNICAL FIELD

The present invention relates to an apparatus for detecting a desired specific component in a biological gas by using gas sensors without separating the gas, and calculating concentration of the component. Also, the present invention relates to a method for detecting a desired specific component in a biological gas in which interference gas components coexist by using gas sensors without separating the gas, and calculating concentration of the component.

BACKGROUND ART

Conventionally, some techniques have been discussed for obtaining and grasping biological information, typically health condition of a living body, by measuring and analyzing biological gas components released from the living body. For example, Patent Document 1 and Patent Document 2 disclose techniques for detecting diabetes and measuring the degree of combustion of body fat by detecting a concentration of acetone included in an expiration gas. Also, Patent Document 3 discloses a technique for detecting abnormal proliferation of intestinal anaerobic bacteria and malabsorption syndrome by sensing hydrogen included in an expiration gas. Also, Patent Document 4 and Patent Document 5 disclose techniques for implementing complicated medical examination by detecting several types of gas components in an expiration gas by means of multiple types of gas detection elements for acetone, nitric monoxide, carbon dioxide, hydrogen and ammonia as well as detecting a single gas component in the expiration gas.

Many types of gas components coexist at various concentrations in a biological gas such as the expiration gas. In a case where a specific gas component is measured (detected and/or concentration is calculated) without separating these gas components, there is a problem in that they interfere with each other and the desired gas component cannot be measured correctly. For this problem, a gas chromatography method is widely known for measuring each gas component by separating them. However, in general, the apparatus is large, and the operation method requires proficiency. Thus, the chromatography method is not appropriate for simple use.

Also, for this problem, techniques are known for selecting and using gas sensors that react selectively and specifically for respective biological gas components (patent documents 1, 3, 4 and 5, for example). However, it is practically difficult to find a sensor with which other gas components do not interfere at all, and, in the case where such selective and specific gas sensors are used, there is a possibility in that measured concentration becomes inaccurate when the concentration of the interference gas component is high. Further, since there are many types of biological gas components, in the biological gas, which can be used for health diagnosis and disease determination, it is difficult and impractical to prepare as many gas sensors, that specifically react particular biological gas components, as the types of biological gas components (Patent Document 6, for example).

PRIOR ART DOCUMENTS

[Patent document 1] JP2002-31615
[Patent document 2] JP2001-349888
[Patent document 3] JP2006-75447
[Patent document 4] JP2009-257772
[Patent document 5] JP2010-26746
[Patent document 6] JP5-203598

SUMMARY OF THE INVENTION

Problem to be Solved by the Invention

An object of the present invention is to provide an apparatus and a method that can solve the above-mentioned problem and that can easily detect a desired specific component in a biological gas released from a living body and calculate concentration of the component, even when interference gas components coexist, without separating the gas by using a small number of types of gas sensors, so that anybody can check health status or results of diet anywhere at anytime.

Means for Solving the Problem

To achieve the above-mentioned object, a biological gas detection apparatus of the present invention is a biological gas detection apparatus including:
a sensor unit including plural types of gas sensors;
a control unit of the sensor unit;
a data recording unit; and
a data analyzing unit,
wherein the data recording unit includes a database on properties of sensitivities of the gas sensors for a single body of a desired gas component, a single body of an interference gas component, and a mixed gas of these that are included in the biological gas, and
the data analyzing unit calculates concentration of the desired gas component based on sensitivities of the gas sensors output when detecting the biological gas and the database.

Also, a biological gas detection method of the present invention is a biological gas detection method performed by a biological gas detection apparatus including:
a sensor unit including plural types of gas sensors;
a control unit of the sensor unit;
a data recording unit; and
a data analyzing unit,
wherein the data recording unit includes a database on properties of sensitivities of the gas sensors for a single body of a desired gas component, a single body of an interference gas component, and a mixed gas of these that are included in the biological gas, and
the data analyzing unit calculates concentration of the desired gas component based on sensitivities of the gas sensors output when detecting the biological gas and the database.

Effect of the Present Invention

According to an embodiment of the present invention, in measurement of biological gas components released from a living body, an apparatus is provided for detecting a desired specific biological gas component and calculating concentration of the component, even in the presence of interference gas components, by using plural types of gas sensors without the need of separating the biological gas components, and a method is provided for detecting a desired specific biological gas component and calculating concentration of the component in consideration of effects of interference gas components, so that anybody can easily check health status or results of diet anywhere at anytime.

BRIEF DESCRIPTION OF THE DRAWINGS

FIG. 6 is a list showing types of pseudo expiration gas and measurement results of sensor sensitivity in accordance with an example;

FIG. 11 is a list showing types of actual expiration gas and measurement results of sensor sensitivity in accordance with an example;

EMBODIMENTS FOR CARRYING OUT THE INVENTION

Figure 1:
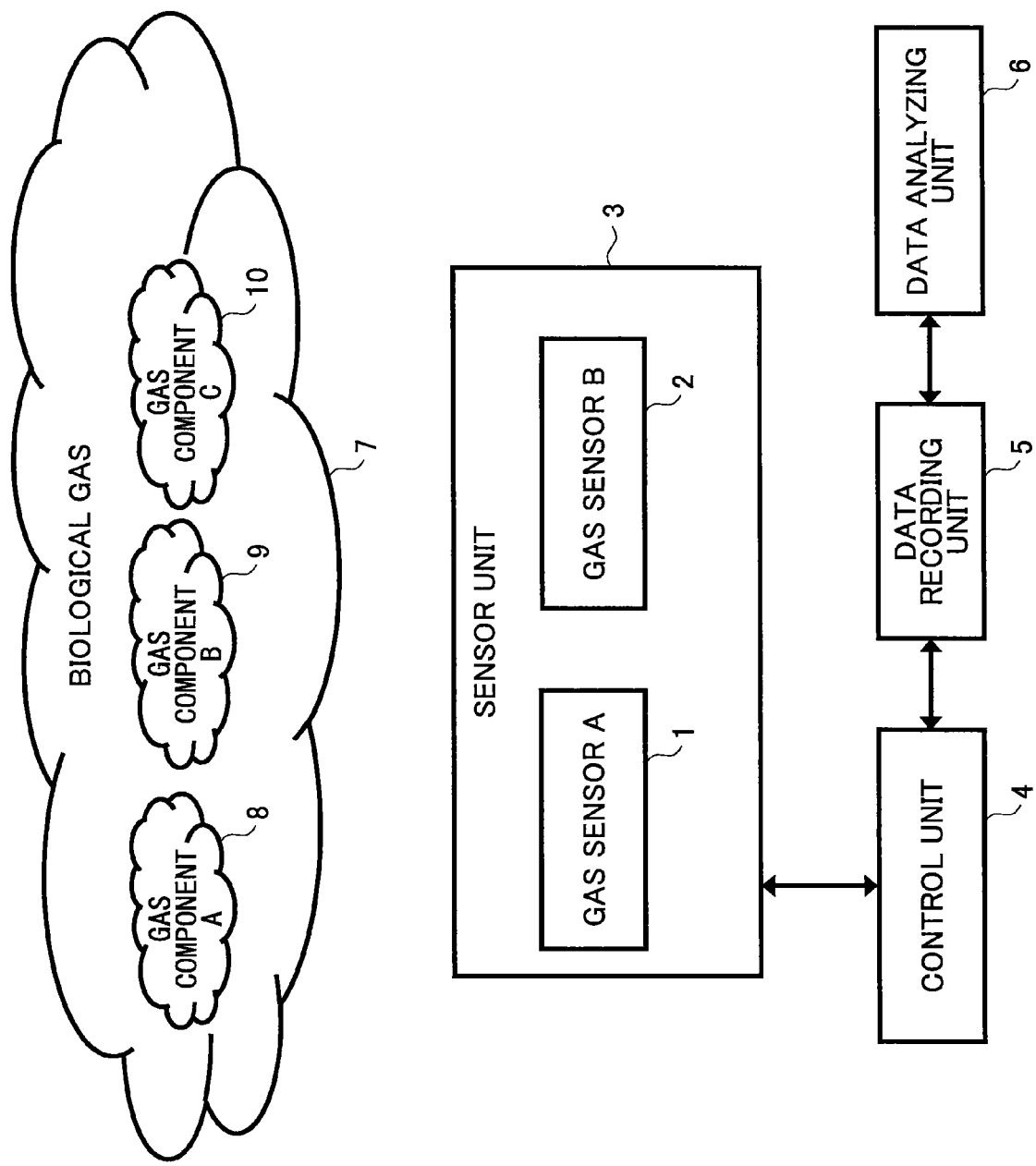
FIG. 1 is a schematic diagram showing a biological gas detection apparatus according to an embodiment of the present invention.

An embodiment of the present invention is for detecting a desired specific component in a biological gas released from a living body, and calculating the concentration of the specific component, even when interference gas components coexist, without separating the gas by using a small number of gas sensors.

The gas released from a living body means a component egested from various biochemical pathways in the living body to an outside of the living body. More particularly, egestion to the outside of the living body includes egestion from the lung into expiration by breathing, egestion from stomach and intestines and the like via esophagus and mouth and the like. The gas or the gas component is not necessarily limited to a gaseous matter in a normal temperature and pressure condition (1 atmospheric pressure, 25° C., for example), and includes a component egested in a gaseous state with other gas component or fluid egested to the outside of the living body at the same time. Also, the biological gas components include inorganic gas components and organic gas components. The inorganic gas components include hydrogen, ammonia, nitric monoxide and the like, for example. The organic gas components include acetone, aldehyde, alcohol and the like. In an embodiment of the present invention, a biological gas component to be detected and for which concentration is to be calculated is regarded as a desired specific component (or desired gas component). For example, in an example, the desired specific component is described as acetone. Further, in an embodiment of the present invention, a coexisting gas component other than the desired component is described as an interference gas. However, the interference gas meant here not only includes a gas component that strongly interferes with detection and concentration calculation for the desired gas component, but also includes a component that weakly interferes or a gas component that does not interfere at all. The reason is that interference action and phenomenon depend on types of sensors to be used, types of biological gases, presence concentration, detection conditions (temperature, for example) and the like.

In addition, in the apparatus and the method of an embodiment of the present invention, even though the above-mentioned interference gas components coexist, detection can be easily made and the concentration is calculated by using a small number of types of gas sensors without separating the biological gas. "Without separating" means that at least the desired gas component is separated from other gas components so as to remove interference actions (or the possibility) but does not mean that every gas component is separated. In an embodiment of the present embodiment, it is possible to measure biological gas released from a living body, as it is or by concentrating or attenuating it using proper other method, so as to detect a desired gas component and calculate the concentration of the gas component. Also, in an embodiment of the present invention, on the premise of the presence of interference action, a small number of types of gas sensors are used. That is, in the embodiment of the present invention, it is not necessary to use the same number of specific/selective gas sensors, corresponding to gas components included in the biological gas respectively, as the number of the biological gas components.

Usable gas sensors in the embodiment of the present invention are sensors that can be selected properly from various types of gas sensors that are generally known. As an example, in an embodiment of the present invention, general-purpose gas sensors can be used. As the usable gas sensor in the embodiment of the present invention, an optimum sensor can be properly selected from known sensors based on types and concentration range of components to be detected (desired gas component, interference gas component, and other gas component such as fluid), detection limit, detection condition and the like, or an optimum sensor can be obtained by modifying an already known sensor. For example, in gas components that may be included in the expiration gas, for example, acetone can be considered as the desired gas component, and alcohol, hydrogen and the like can be considered as possible interference gas components, and it is preferable to select from among maintenance-free semiconductor sensors that can be used repeatedly. Further, in many cases, the concentration of gas components included in the expiration gas is low, thus, it is preferable to use the semiconductor gas sensor having high detection capability for the detection target gas component. The "high detection capability" means that, even though concentration of a gas component that is a detection target is low, the concentration can be identified.

Further, in an embodiment of the present invention, at least two types of sensors are used even though equal to or greater than two types of interference gas components coexist with the desired gas component. These two types of sensors may be gas sensors. In an embodiment of the present invention, although there is no restriction for selecting the sensors, it is preferable to select a first senor, of the at least two types of sensors, that has high detection capability mainly for the desired gas component, and a second sensor that has detection capability at least for an interference gas component and that has gas-sensing properties different from the first sensor. By the above-mentioned selection, as described below, it is possible to easily find an algorithm for detecting the desired gas component and calculating the concentration of the gas component. In the following, an apparatus of an embodiment of the present invention is described concretely.

FIG. 1 is a schematic diagram showing an embodiment of a biological gas detection apparatus of the present invention. The sensor unit 3 is provided with a gas sensor A and a gas sensor B. Each of the sensors A and B is controlled by a control unit 4. Further, the control unit 4 is connected to a data recording unit 5 and a data analyzing unit 6. The gas sensor A is a gas sensor having relatively higher detection capability for the desired specific gas component. The gas sensor B has detection capability at least for the interference gas component, and indicates gas-sensing properties different from the gas sensor A. Here, as an example, the gas sensor has almost the same detection capability for the desired gas component and the interference gas component. In this embodiment, although a case where two gas sensors are used is described in order to describe the embodiment more clearly and simply, the present invention is not limited to the number, and the number of the gas sensors may be equal to or greater than 2.

A biological gas 7 is introduced to the sensor unit 3 so that biological gas components 8, 9 and 10 are detected at the same time or separately and data is output by the gas sensors A and B. The output data is displayed on the sensor unit or output from the sensor unit so that the data is recorded and analyzed as described below.

In FIG. 1, the gas sensors A and B are controlled by the control unit 4. Detection operation by the gas sensors A and B, and output data from the sensors are controlled by the control unit 4. In addition, the control unit 4 sends the output data to the data recording unit 5 so that the data is recorded. The output data may be directly output to the data recording unit 5 without using the control unit 4. The recorded data is analyzed by the data analyzing unit 6 so as to calculate the concentration of the desired specific gas component, and concentration of interference gas components as necessary.

The data analyzing unit 6 calculates sensitivity of each of the gas sensors A and B for the gas of measurement target, and calculates concentration of the gas. The sensitivity of the gas sensor is calculated as a ratio (R/Rair) between R and Rair in which Rair is a resistance of the gas sensor in the air, and R is a resistance of the gas sensor when the measurement target gas is blown. In the following description, R/Rair is defined and used as the sensitivity for convenience. However, the calculation method of the sensitivity is not limited to this method, and there may be a case where condition for size comparison with the threshold in the concentration calculation algorithm described below is reversed depending on the method.

In each of the gas sensor A and the gas sensor B of the present embodiment, as reductive gas concentration increases, the resistance value and the value of the sensitivity (R/Rair) of the sensor decrease. As an example, each of the gas sensor A and the gas sensor B is a semiconductor gas sensor using an n-type semiconductor. However, the gas sensor of the present invention is not limited to the gas sensor of such properties. As the reductive gas concentration increases, the resistance value and the value of the sensitivity of the sensor may increase.

In the calculation method of gas concentration, based on the obtained sensitivity of the gas sensor, a pre-recorded database (FIG. 2-FIG. 4) representing relationship between sensitivity and concentration is used. The database to be used is not limited to the one representing relationship between sensitivity and concentration. The database may be one representing sensitivity of each sensor, sum of sensitivities of sensors, ratio of sensitivities between sensors, or relationship between these and concentration, and the like, for example.

The database to be pre-recorded may be recorded in any of the control unit 4, the recording unit 5 and the data analyzing unit 6. The database includes sensitivity behavior of the sensors A and B for desired gas component, interference gas component, and a mixture gas of the desired gas component and the interference gas component. More specifically, the database includes relationship between each single body gas of the interference gas component or the desired gas component and each sensor sensitivity, effects of mixture ratio of the interference gas component with respect to the desired gas component for the sensor sensitivity, and the like. Further, the database may include other parameters derived from the sensitivity behaviors. More specifically, it is assumed that sensitivities of the gas sensors A and B when the gas sensors A and B are exposed to a biological gas are $\alpha$ and $\beta$ respectively. Also, it is assumed that a ratio E of sensitivities of the gas sensors A and B is defined as $E=\alpha/\beta$. In an embodiment of the present invention, the database representing the relationship among $\alpha$, $\beta$, and E is created beforehand, and an algorithm is prepared and created for calculating and estimating concentration of a desired gas component (gas component A) in consideration of effects of the interference gas components (gas component B, gas component C) by using all or a part of the values of the database.

The data analyzing unit 6 finds the algorithm by referring to the created database based on the values of $\alpha$, $\beta$ and E obtained for a biological gas by actual measurement, and calculates concentration of the desired gas component in consideration of effects of interference gas components.

FIG. 1 shows an example including, as a biological gas, three types of gases that are a gas component A, a gas component B and a gas component C. In this example, the desired gas component is A, and the interference gas components are B and C. Of course, although actual biological gas components include quite a lot of types of gas components, instead of three types, a case where the number of biological gas components is three is described here for convenience of simplicity.

By exposing the gas sensor A and the gas sensor B in the sensor unit 3 to the biological gas including the gas component A, the gas component B and the gas component C, sensitivities of the gas sensor A and the gas sensor B change. In this case, the sensitivity change of the gas sensor A is largely due to effects of the gas component A, but, effects of gas components B and C cannot be neglected for biological gas measurement at ppm-ppb level required for health diagnosis and disease diagnosis using the biological gas.

It is assumed that sensitivities of the gas sensors A and B when the gas sensors A and B are exposed to the biological gas are $\alpha$ and $\beta$ respectively. Also, it is assumed that the ratio E of sensitivities of the gas sensors A and B is $E=\alpha/\beta$. As described above, a database representing relationship among $\alpha$, $\beta$ and E is created beforehand, and an algorithm is prepared and created for calculating and estimating concentration of the desired gas component (gas component A) in consideration of effects of interference gas components (gas component B, gas component C) by using a part or all of these values.

Based on that, as described below, the database is referred to by using the algorithm based on actually measured values of α, β and E for the biological gas, so as to calculate the concentration of the desired gas component in consideration of the effects of the interference gas components.

(1) If the sum of the sensitivity of the gas sensor A and the sensitivity of the gas sensor B is greater than a predetermined first threshold, it is determined that the concentration of the desired gas component is very low as though the desired gas component can be regarded as being absent, or there is a problem during measurement.

(2) If the sensitivity of the gas sensor B is greater than a predetermined second threshold, the concentration of the desired gas component is calculated based on the sensitivity of the gas sensor A and the database.

(3) If the sensitivity of the gas sensor B is equal to or less than the predetermined second threshold and a sensitivity ratio of the gas sensor A and the gas sensor B is greater than a predetermined third threshold, the concentration of the desired gas component is calculated based on the sensitivity of the gas sensor A and the database.

(4) If the sensitivity of the gas sensor B is equal to or less than the predetermined second threshold and the sensitivity ratio of the gas sensor A and the gas sensor B is equal to or less than the predetermined third threshold, the concentration of the interference gas component is calculated based on the sensitivity of the gas sensor B and the database, and the concentration of the desired gas component is calculated based on the interference gas component concentration, the sensitivity of the gas sensor A, and the database.

In a case where detection capability of the gas sensor A is particularly high with respect to the desired gas component, the algorithm can be simplified as follows.

(1) If the sensitivity of the gas sensor B is greater than a predetermined fourth threshold, the concentration of the desired gas component is calculated based on the sensitivity of the gas sensor A and the database.

(2) If the sensitivity of the gas sensor B is equal to or less than a predetermined fourth threshold and the sensitivity of the gas sensor A is equal to or less than a predetermined fifth threshold, the concentration of the desired gas component is calculated based on the sensitivity of the gas sensor A and the database.

(3) If the sensitivity of the gas sensor B is equal to or less than the predetermined fourth threshold and the sensitivity of the gas sensor A is greater than the predetermined fifth threshold, the concentration of the interference gas component is calculated based on the sensitivity of the gas sensor B and the database, and the concentration of the desired gas component is calculated based on the interference gas component concentration, the sensitivity of the gas sensor A, and the database.

Figure 5:
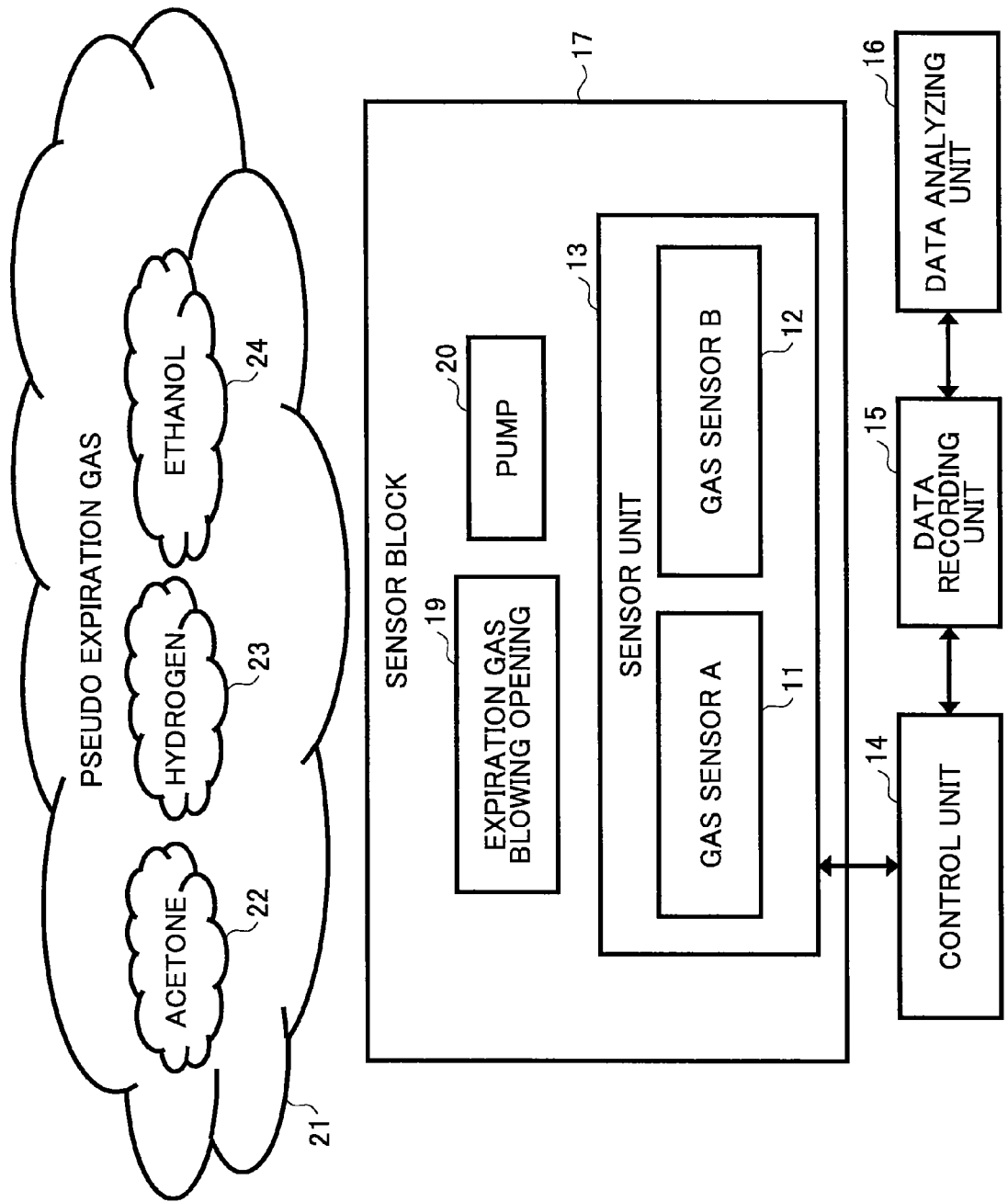
FIG. 5 shows a configuration example of an expiration gas detection apparatus in accordance with an example.

FIG. 5 schematically shows an embodiment in which, in addition to the above-described apparatus of the embodiment of the present invention, a sensor block 17 including a sensor unit 13 is provided, and this apparatus was used in an example described below. In this example, an expiration gas blowing opening 19 and a pump 20 (biological gas introducing unit) are provided in order to introduce the biological gases 22, 23 and 24 to the sensor unit 13 including the sensors A and B accurately and quickly. But, the pump 20 is not necessarily essential, and may be provided when gas replacement in the sensor unit needs to be performed especially quickly. The biological gases 22, 23 and 24 are introduced in the sensor unit 13 from the expiration gas blowing opening 19, so that each component of the biological gases is detected by the gas sensors A and B and has effects on each sensor sensitivity.

Accordingly, the desired gas component of the biological gas can be detected accurately and quickly, and the concentration of the desired gas component can be calculated.

In the following, the present invention is described in more detail based on an example. But, the present invention is not limited to the example.

EXAMPLE

In this example, the biological gas is assumed to be an expiration gas, and acetone included in the expiration gas is the desired gas component. Also, it is assumed that ethanol and hydrogen included in the expiration gas are interference gas components.

Each of the gas sensors A and B used in the example is a semiconductor-type gas sensor made by FIS Inc. In the measurement, each sensor was exposed to the air for three minutes and was read as Rair, and the measurement gas described below was similarly blown quietly on the sensors for 10 seconds so that the sensors are exposed to the measurement gas, and the resistance value R was read.

[Advance Preparation 1: Creation of Database of Acetone Concentration in a State where there is No Interference Gas Component]

Figure 2:
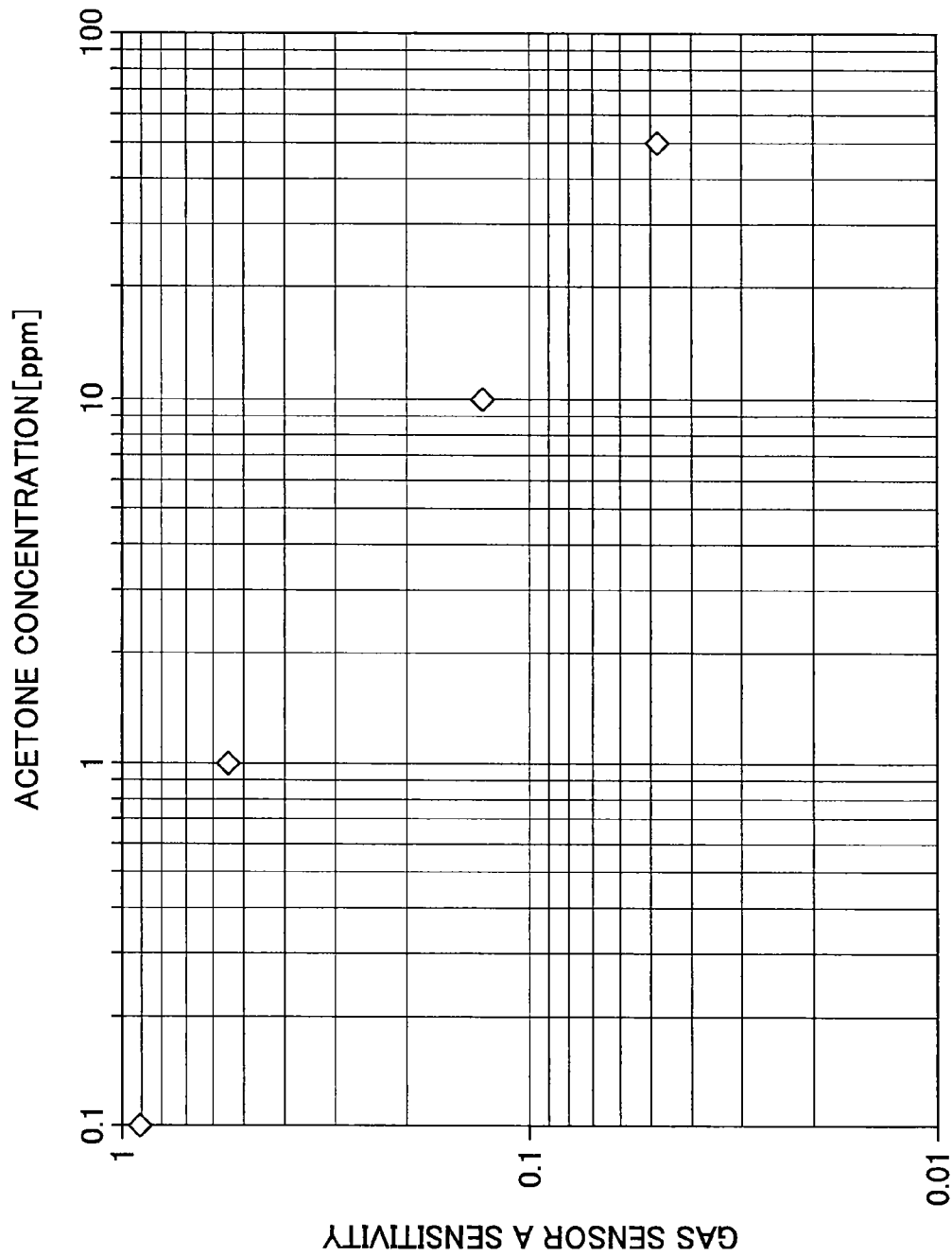
FIG. 2 is a graph (database) showing sensitivity change of the gas sensor A when acetone concentration is changed in accordance with an example.

Sensitivity of the gas sensor A is measured in cases where the acetone concentration is 0.1, 1, 10, and 50[ppm] respectively, and a database of the sensitivity of the gas sensor A and the acetone concentration is created in a case where acetone pure gas in which no interference gas component is included is used. An example of measurement results is shown in FIG. 2.

[Advance Preparation 2: Creation of Database of Acetone Concentration in the Presence of Ethanol]

Figure 3:
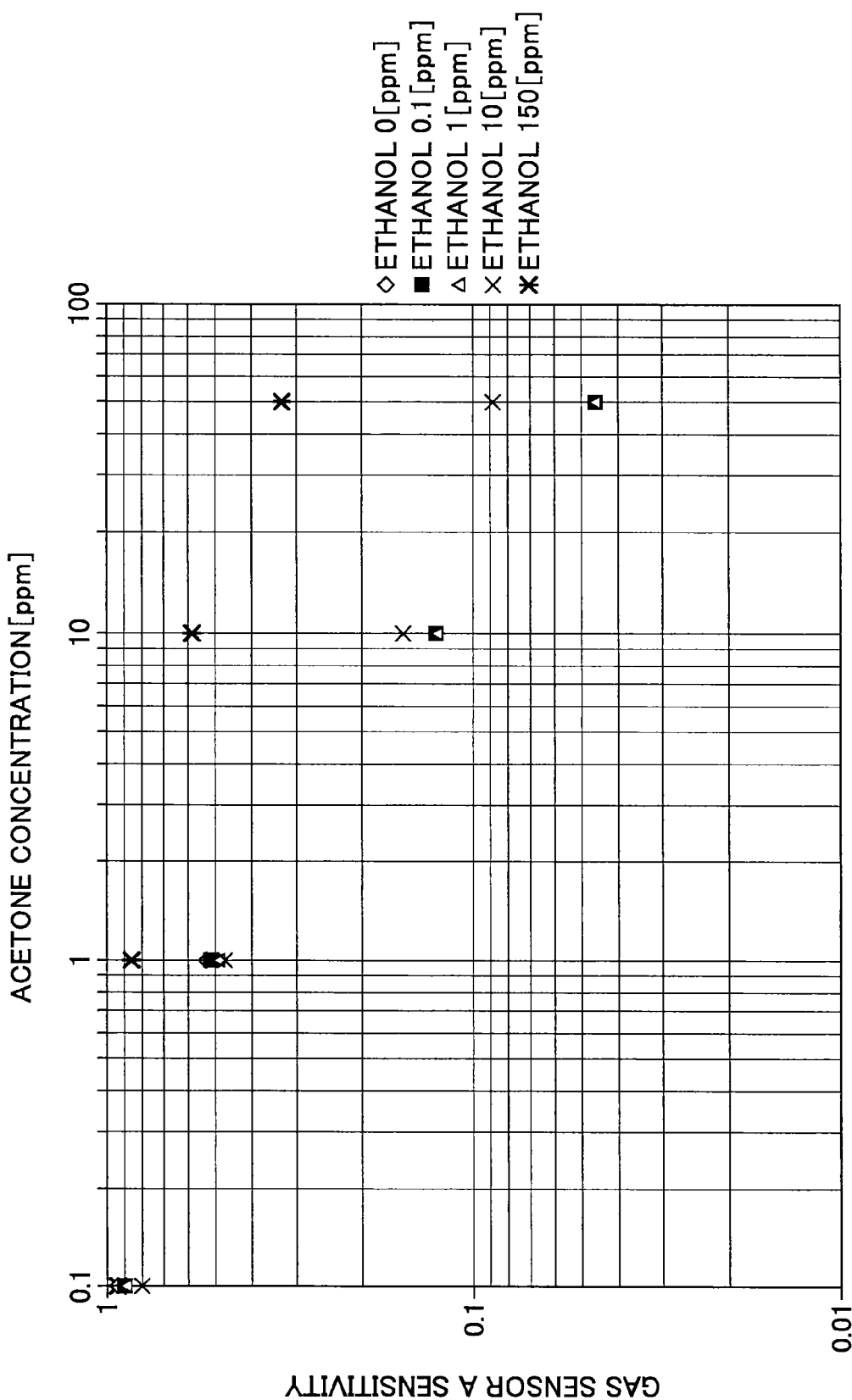
FIG. 3 is a graph (database) showing sensitivity change of the gas sensor A when acetone concentration is changed in the presence of ethanol in accordance with an example.

Sensitivity of the gas sensor A with respect to acetone concentration in the presence of ethanol is measured, in the presence of a mixture gas of acetone and ethanol in which any one of acetone 0.1, 1, 10, and 50[ppm], and any one of ethanol 0, 0.1, 1, 10, and 150[ppm] are mixed, so that the database of the sensitivity of the gas sensor A and the acetone concentration in the presence of ethanol is created. An example of measurement results is shown in FIG. 3.

[Advance Preparation 3: Creation of Database of Ethanol Concentration in a State where there is No Interference Gas Component]

Figure 4:
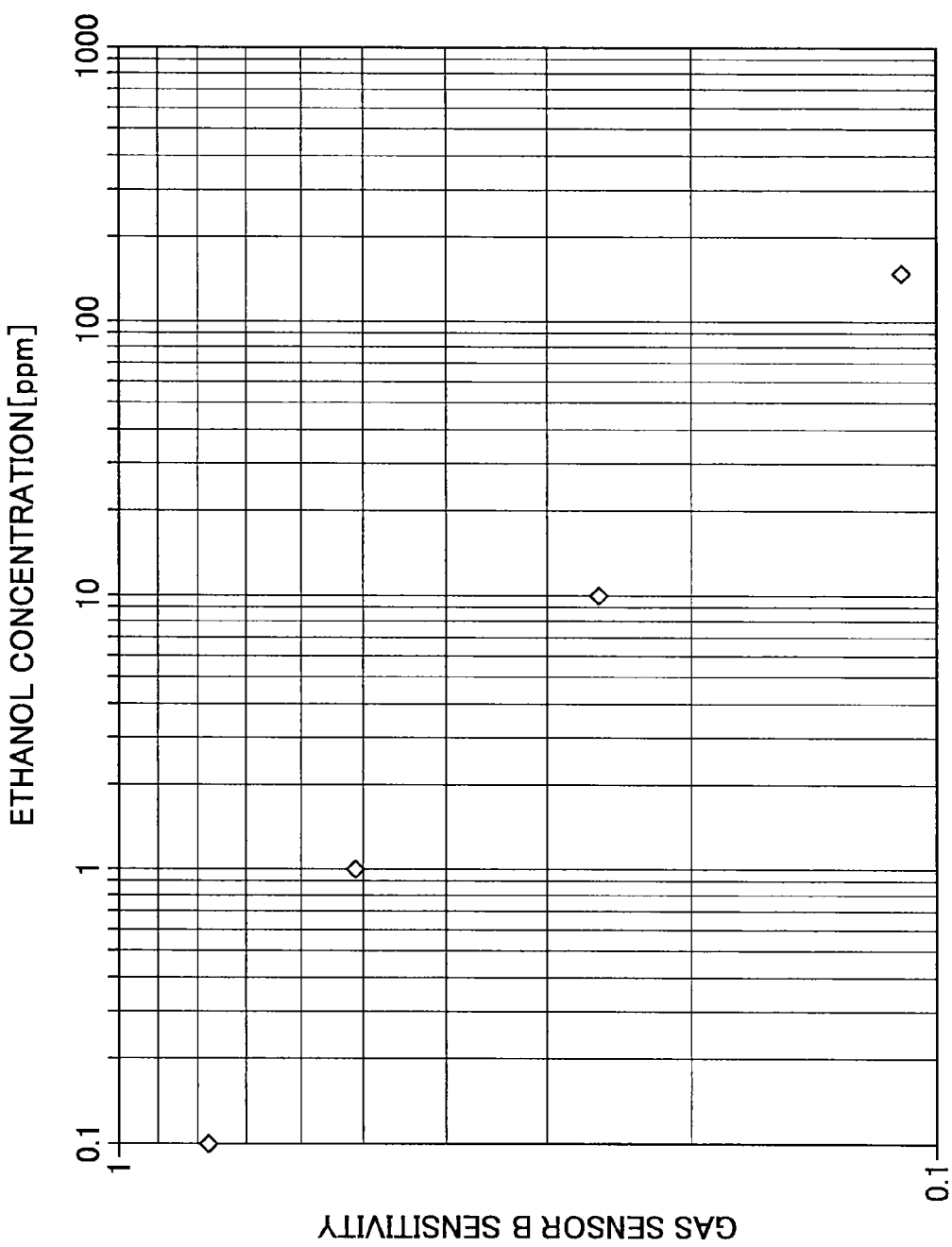
FIG. 4 is a graph (database) showing sensitivity change of the gas sensor B when ethanol concentration is changed in accordance with an example.

Sensitivity of the gas sensor B is measured in cases where the ethanol concentration is 0.1, 1, 10, and 150[ppm] respectively, and a database of the sensitivity of the gas sensor B and the ethanol concentration is created in a case where ethanol pure gas in which no interference gas component is included is used. An example of measurement results is shown in FIG. 4.

[Advance Preparation 4: Creation of Acetone Concentration Estimation Algorithm]

Figure 7:
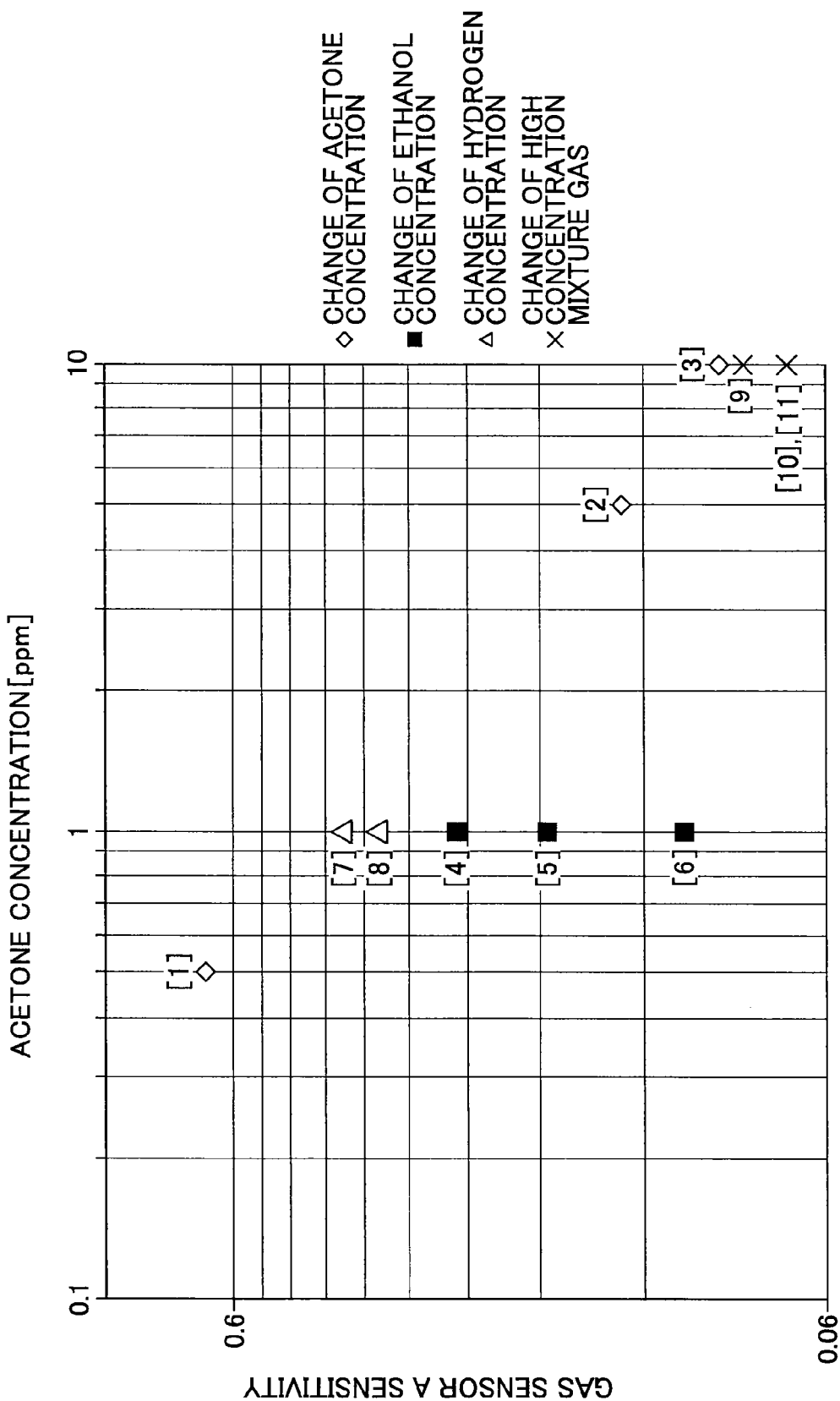
FIG. 7 is a diagram showing sensitivity change of the gas sensor A when acetone concentration is changed in the pseudo expiration gas in accordance with an example.
Figure 8:
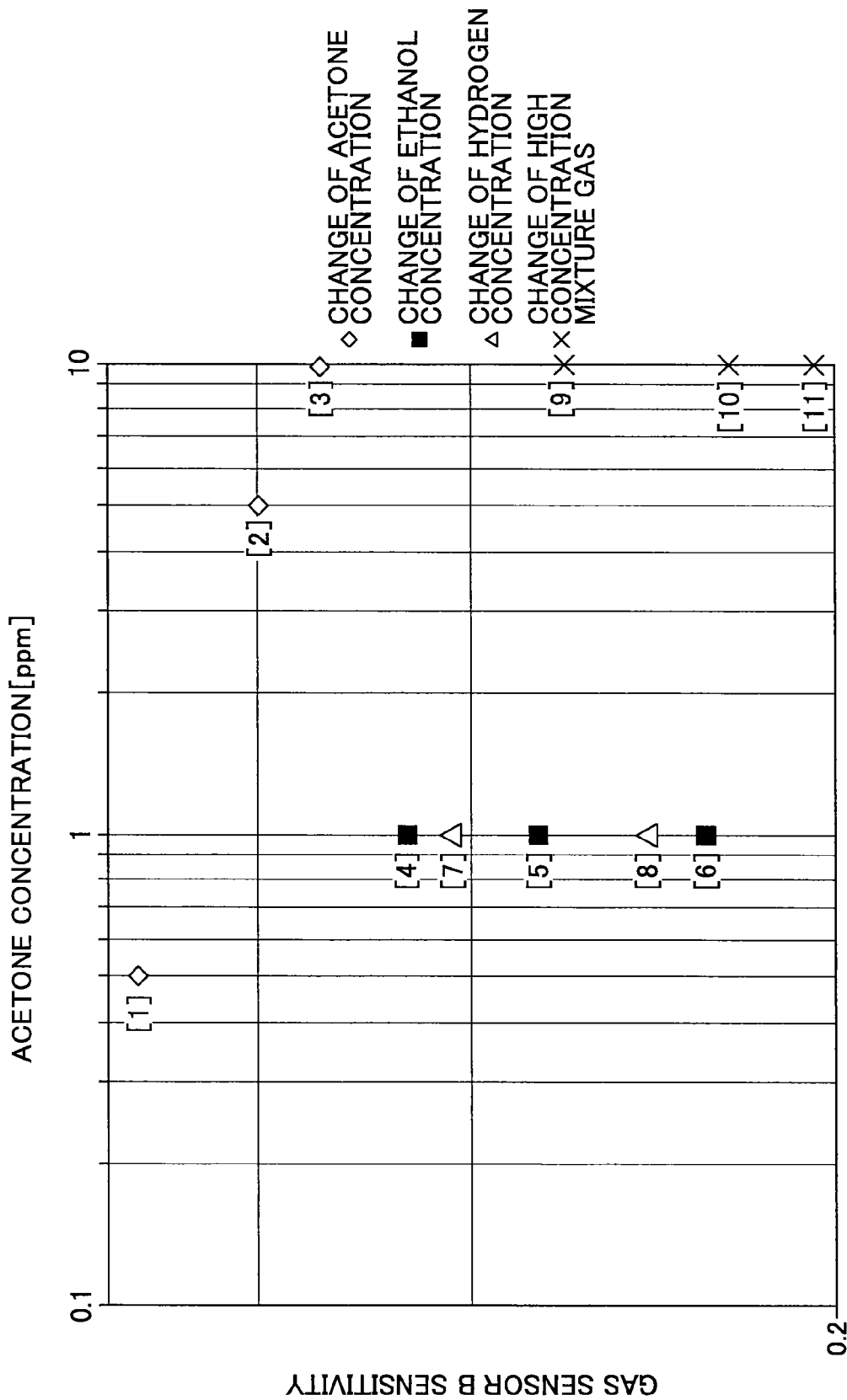
FIG. 8 is a diagram showing sensitivity change of the gas sensor B when acetone concentration is changed in the pseudo expiration gas in accordance with an example.
Figure 9:
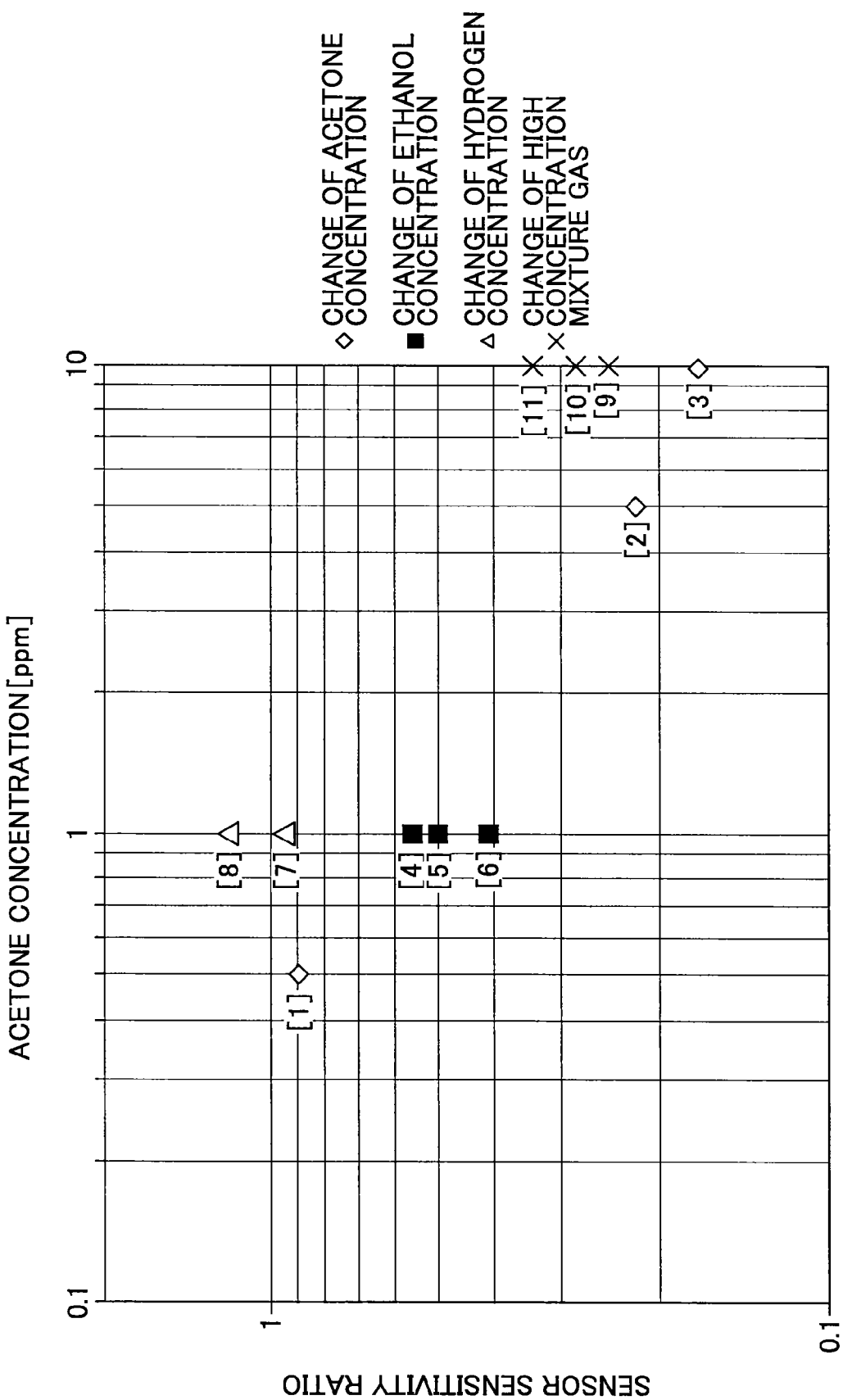
FIG. 9 is a diagram showing sensitivity ratio of gas sensor A and gas sensor B when acetone concentration is changed in the pseudo expiration gas in accordance with an example.

An experiment for measuring acetone concentration was carried out by using the gas sensor A and the gas sensor B in a pseudo expiration gas in which acetone, hydrogen and ethanol were mixed, and an algorithm was created from the experimental result for calculating acetone concentration in consideration of effects of the interference gas components (hydrogen, ethanol). FIG. 6 collectively shows 11 types of pseudo expiration gases used here, sensitivity of gas sensors A and B for these types, ratio of sensitivity of the gas sensor A and sensitivity of gas sensor B, and the sum of the sensitivity gas sensor A and sensitivity of the gas sensor B. FIGS. 7-9 show graphs on which the measurement results of FIG. 6 are plotted. In this example, sensitivity ratio between the gas sensor A and the gas sensor B is represented as E, and E is represented as E=(sensitivity of gas sensor A)/(sensitivity of gas sensor B).

Example 1

<Acetone Concentration Calculation Algorithm>

Figure 10:
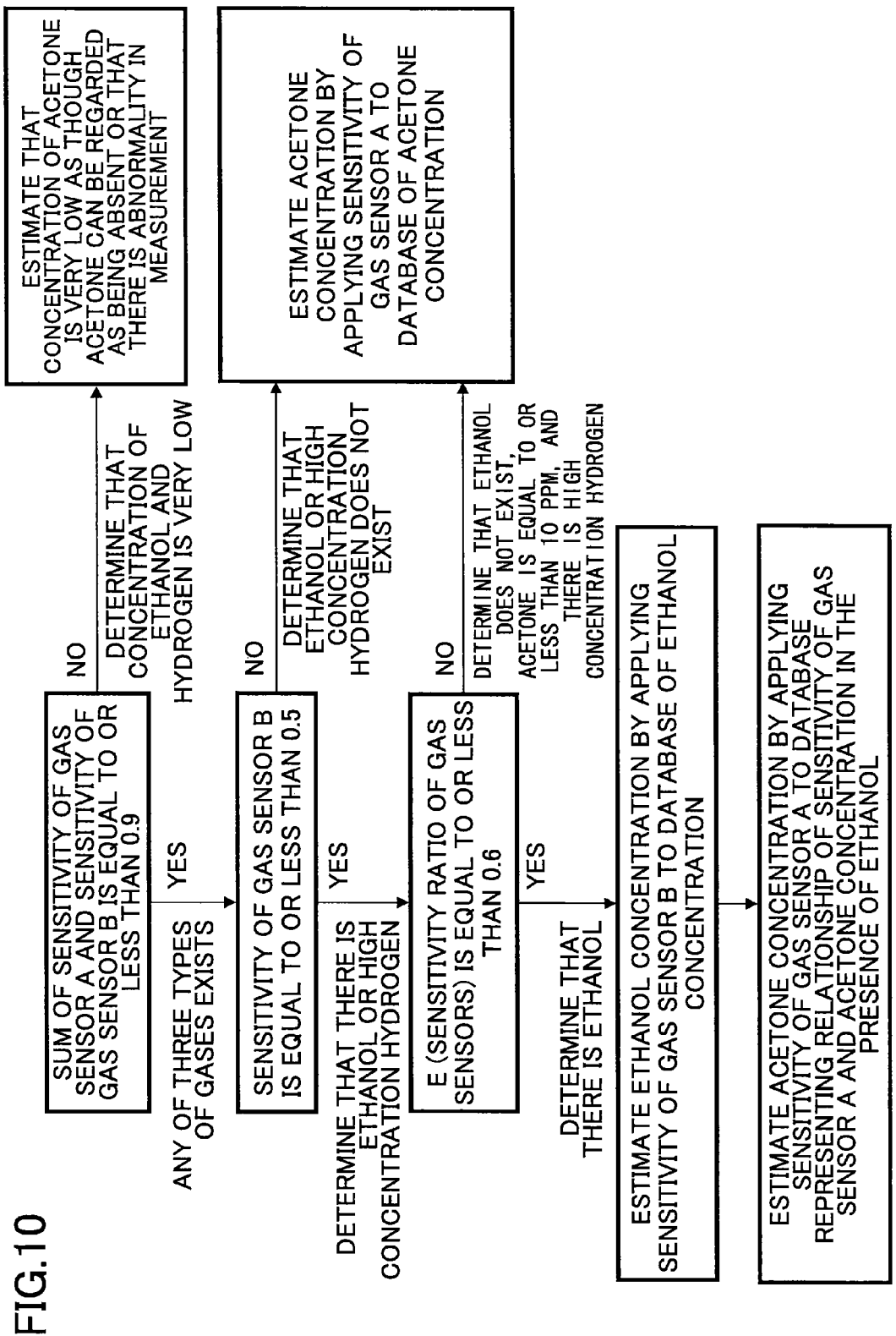
FIG. 10 is a flowchart of a method for calculating acetone concentration in accordance with an example 1.

Base on the above-mentioned measurement data, an acetone concentration calculation algorithm is created as follows (FIG. 10).

(1) When the sum of the sensitivity of the gas sensor A and the sensitivity of the gas sensor B is greater than 0.9: it is determined that the concentration of the hydrogen and the ethanol is very low as though the hydrogen and the ethanol can be regarded as being absent, and, also, it is determined that the concentration of the acetone is very low as though acetone can be regarded as being absent, or there is a problem during the measurement.

(2) When the sum of the sensitivity of the gas sensor A and the sensitivity of the gas sensor B is equal to or less than 0.9:

(I) When the sensitivity of the gas sensor B is greater than 0.5: it is determined that there is very little ethanol or high concentration hydrogen, and the acetone concentration is calculated by applying the sensitivity of the gas sensor A to the database, created from FIG. 2, representing relationship of the sensitivity of the gas sensor A and the acetone concentration in a state where ethanol does not exist.

(II) When the sensitivity of the gas sensor B is equal to or less than 0.5:

(i) When the sensitivity ratio E of the sensors is greater than 0.6: it is determined that the acetone is equal to or less than 10 ppm and there is hydrogen of high concentration. Also, since the effect of the hydrogen to the sensitivity of the gas sensor A is small, the acetone concentration is calculated by applying the sensitivity of the gas sensor A to the database, created from FIG. 2, representing relationship of the sensitivity of the gas sensor A and the acetone concentration in a state where ethanol does not exist by neglecting the effect of the hydrogen.

(ii) When E is equal to or less than 0.6: it is determined that there is ethanol of equal to or greater than certain concentration, and the ethanol concentration is estimated by applying the database, created from FIG. 4, representing relationship of the sensitivity of the gas sensor B and the ethanol concentration, and the acetone concentration is calculated by using the database, created from FIG. 3, representing relationship of the sensitivity of the gas sensor A and the acetone concentration in the presence of ethanol.

[Calculation of Acetone Concentration in an Actual Expiation Gas]

Calculation of the acetone concentration in an actual expiation gas was carried out by using the created acetone concentration estimation algorithm (FIG. 10). FIG. 11 shows 11 types of expiration gases that were measured and results of measurement of sensor sensitivities. For verifying validity of the algorithm, FIG. 11 also shows concentration measurement results of acetone, hydrogen, and ethanol by using a gas chromatography apparatus in which the same expiation gases were used. In the numbers 1-7, expiration gases of test subjects who did not drink alcohol were used. In the numbers 8-11, measurement were performed using expiration gases of test subjects after drinking alcohol. The sensor sensitivity measurement was performed by using the apparatus schematically shown in FIG. 5. The expiation gas was blown into the expiration gas blowing opening 19 that was provided in the sensor block 17 including the sensor unit 13, so that the expiration gas contacted the gas sensors A and B provided in the sensor unit 13. The pump 20 is not necessarily essential, and the pump 20 may be used for exchanging the expiration gas quickly.

Figure 12:
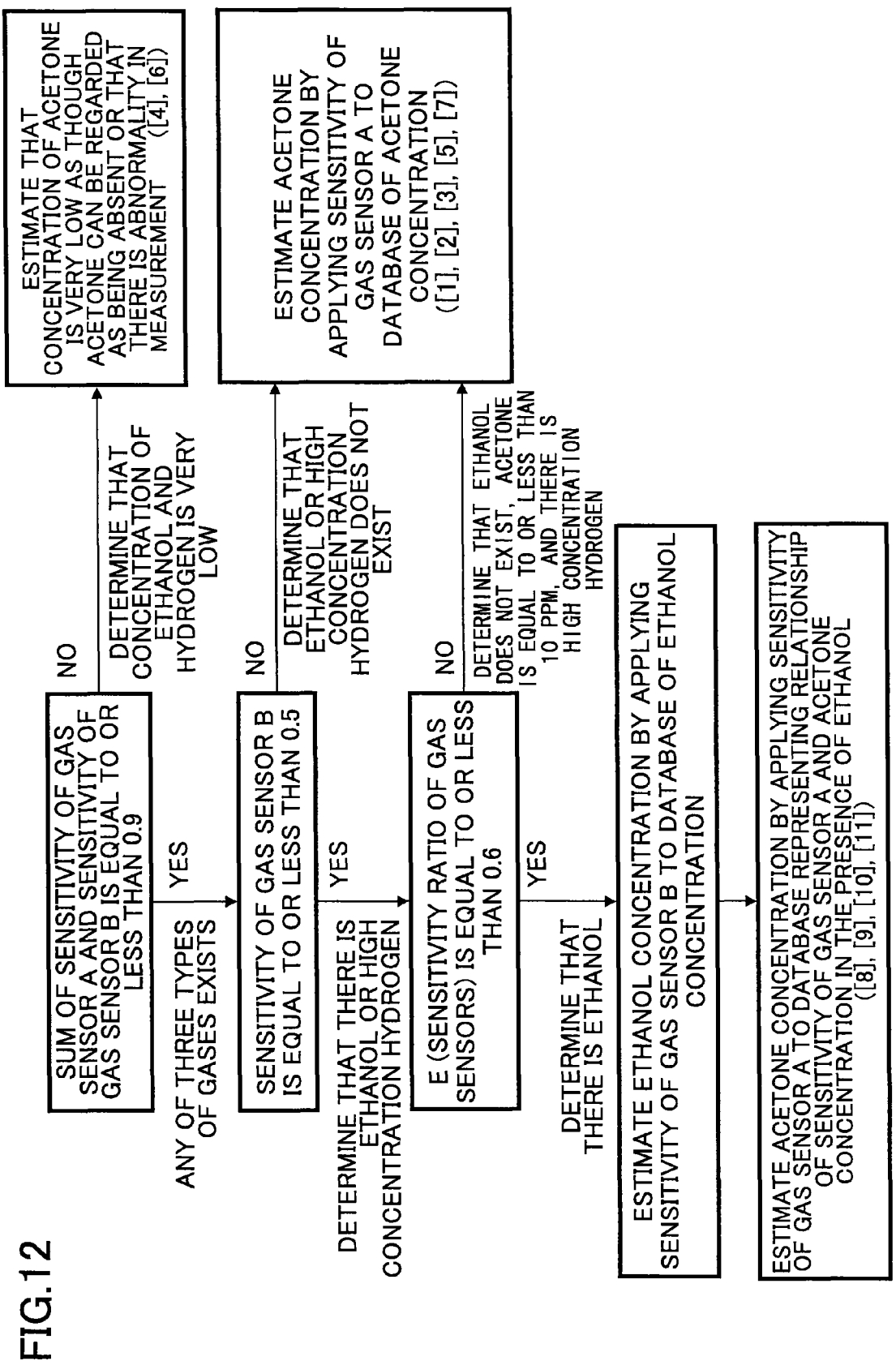
FIG. 12 shows results of carrying out the method for calculating acetone concentration in accordance with the example 1.

FIG. 12 shows results of dividing the 11 types of the expiration gases based on the acetone concentration estimation algorithm (FIG. 10) in accordance with the example 1 of the present invention.

For example, as for the expiration gas of the number 4, since the sum of the sensitivities of the gas sensor A and the gas sensor B is greater than 0.9, it is determined that the concentration of the acetone was very low as though the acetone could be regarded as being absent in the expiration gas, or there was a problem during the measurement. As a result of measuring acetone concentration in the expiration gas by using the gas chromatography apparatus, the concentration was 0.034 ppm, which was very low, indicating that the result was almost the same as the above-mentioned determination result.

For example, as for the expiration gas of the number 3, since the sum of the sensitivities of the gas sensor A and the gas sensor B is equal to or less than 0.9, it is determined that any of the three types of gases exists in the expiration gas. Next, since the sensitivity of the gas sensor B is equal to or less than 0.5, it is estimated that ethanol or hydrogen of high concentration exists. Then, since the sensitivity ratio of the gas sensors is greater than 0.6, it is determined that ethanol does not exist, the acetone is equal to or less than 10 ppm, and hydrogen is in high concentration. By applying 0.44 which is the sensitivity of the gas sensor A into the database of FIG. 2 representing the relationship of the acetone concentration in the state where no interference gas component exists, the acetone concentration is calculated as 0.74 ppm. The result of measurement of the acetone concentration of the expiration gas by using the gas chromatography apparatus is 0.70 ppm which is almost the same as the calculation result.

As for the expiration gas of the number 10, since the sum of the sensitivities of the gas sensor A and the gas sensor B is equal to or less than 0.9, it is determined that any of the three types of gases exists in the expiration gas. Next, since the sensitivity of the gas sensor B is equal to or less than 0.5, it is determined that ethanol or hydrogen of high concentration exists. Then, since the sensitivity ratio of the gas sensors is equal to or less than 0.6, it is determined that ethanol exists. According to these, by applying the sensitivity of the gas sensor B into the database of FIG. 4 representing the ethanol concentration in the state where no interference gas component exists, the ethanol concentration is calculated. Then, the acetone concentration is calculated by applying the estimated ethanol concentration to the database of FIG. 3 representing relationship of the acetone concentration in the presence of ethanol. In the case of this expiration gas, the acetone concentration is calculated as 0.964 ppm. This concentration value is very close to 0.843 ppm which is a result of measuring the acetone concentration of the expiration gas by using the gas chromatography apparatus.

As described above, it can be understood that the acetone concentration estimation algorithm of the example of the present invention has validity.

Example 2

<Simplified Acetone Concentration Calculation Algorithm>

Figure 13:
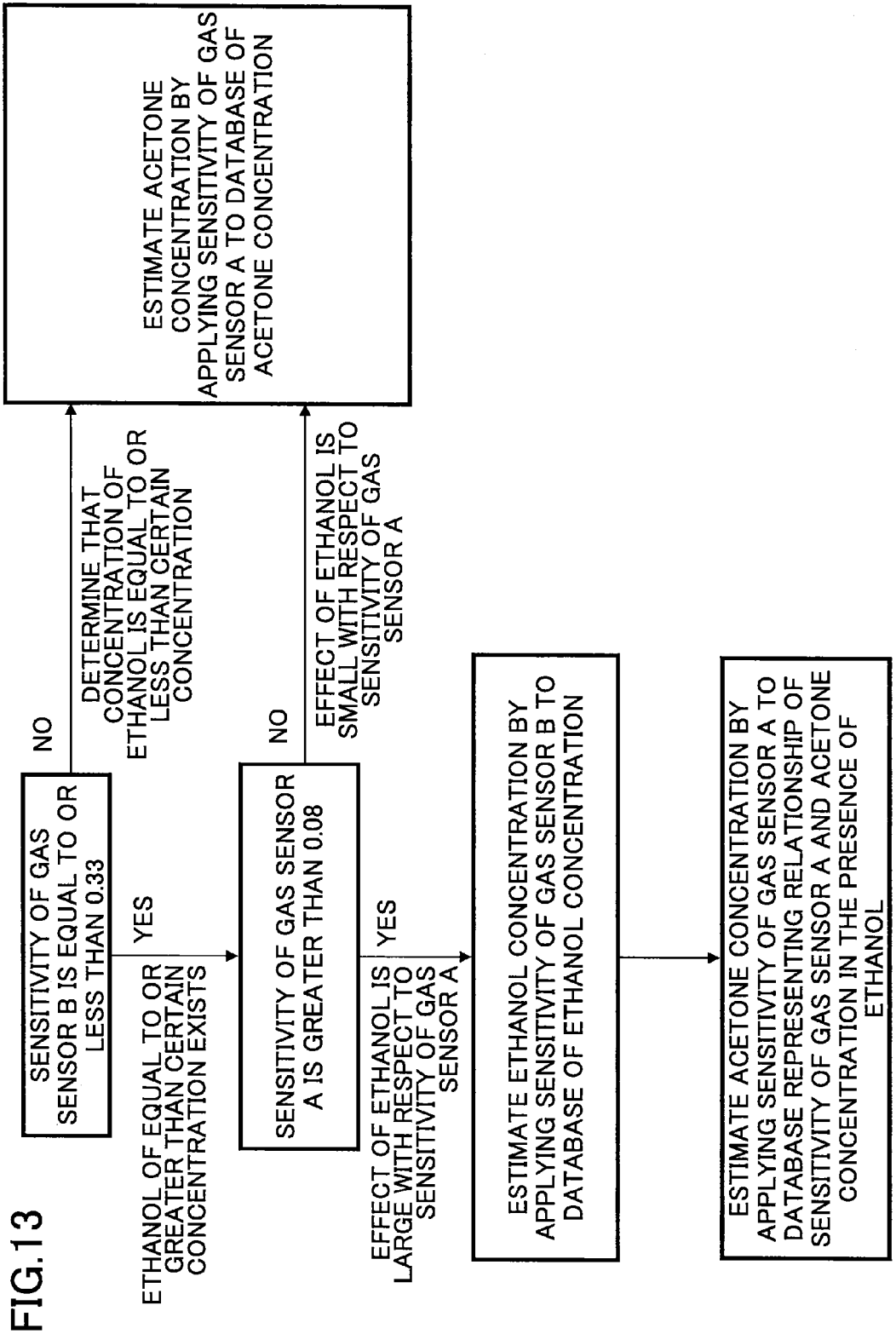
FIG. 13 is a flowchart of a method for calculating acetone concentration in accordance with an example 2.

In a case where the gas sensor A is a gas sensor having especially high detection capability for acetone, the above-mentioned acetone concentration algorithm may be simplified as follows (FIG. 13).

(1) When the sensitivity of the gas sensor B is greater than 0.33: it is determined that either ethanol or hydrogen of high concentration scarcely exists, and the acetone concentration is calculated by applying the sensitivity of the gas sensor A into the database, created from FIG. 2, representing the relationship between the sensitivity of the gas sensor A and the acetone concentration in a state where ethanol does not exist.

(2) When the sensitivity of the gas sensor B is equal to or less than 0.33:
  (I) When the sensitivity of the gas sensor A is equal to or less than 0.08: it is determined that, although ethanol of equal to or greater than certain concentration exists, effect on the gas sensor A is small, so that the effect of the ethanol is neglected. Also, since the effect of the hydrogen on the sensitivity of the gas sensor A is small, the effect of the hydrogen is also neglected. The acetone concentration is calculated by applying the sensitivity of the gas sensor A into the database, created from FIG. 2, representing the relationship between the sensitivity of the gas sensor A and the acetone concentration in a state where ethanol does not exist.
  (II) When the sensitivity of the gas sensor A is greater than 0.08: it is determined that ethanol of equal to or greater than certain concentration exists, and the ethanol concentration is estimated by using the database, created from FIG. 4, representing the relationship between the sensitivity of the gas sensor B and the ethanol concentration. And, the acetone concentration is calculated by using the database, created from FIG. 3, representing the relationship between the sensitivity of the gas sensor A and the acetone concentration in the presence of ethanol.

Figure 14:
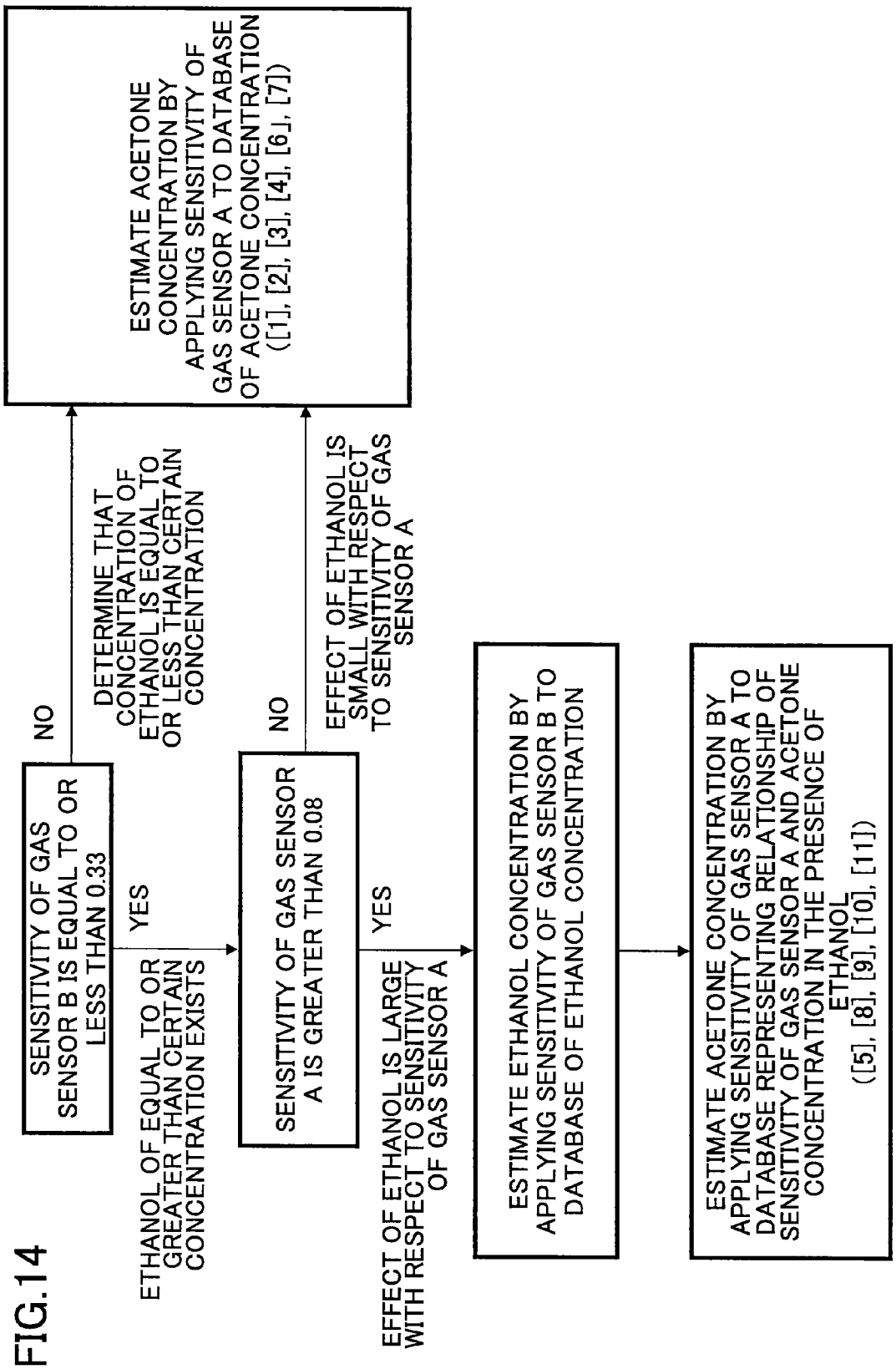
FIG. 14 shows results of carrying out the method for calculating acetone concentration in accordance with the example 2.

FIG. 14 shows results of dividing the 11 types of the expiration gases based on the simplified acetone concentration estimation algorithm (FIG. 13) in accordance with the example 2 of the present invention. Other than the expiration gas of the number 5, the same results as the results (FIG. 12) obtained by applying the not-simplified acetone concentration calculation algorithm were obtained, which indicates that, even though the algorithm is simplified, the algorithm has a measure of validity.

Modified Example 1

As for the apparatus of the embodiment of the present invention, it is possible that functions of power supply to the apparatus of the embodiment of the present invention, the data recording unit and the data analyzing unit are provided in a side of a mobile phone by embedding the apparatus in the mobile phone or by directly connecting the apparatus to the mobile phone via a microUSB and the like. Also, it is possible to display the measurement result on a display device of the mobile phone. By adopting such configurations, the apparatus of the embodiment of the present invention can be easily used, and health conditions and results of diet can be checked anytime and anywhere.

Modified Example 2

Also, it is possible to provide the apparatus of the embodiment of the present invention with a communication function such as Bluetooth, a wireless LAN and the like. By adopting such a configuration, health conditions and results of diet obtained by the apparatus of the embodiment of the present invention can be displayed on a mobile phone or a personal computer by communicating with the mobile phone, for example.

Modified Example 3

In the modified examples 1 and 2, it is also possible to provide a server or the like on a network with all or a part of functions of the data recording unit and the data analyzing unit. According to this configuration, it becomes possible to transfer data of the sensor sensitivity according to the embodiment of the present invention to a server or the like on a network in realtime, as necessary, and to cause the server to record the data or to analyze the data. Thus, by reporting the result to (or displaying the result on) the mobile phone as necessary, a system can be realized for health management, health advice, diet management, diet effect checking service or the like Modified Example 4

In addition, by using the apparatus of the embodiment of the present invention, an expiration gas diagnostic apparatus can be configured. For example, by finding relationship between values of concentration of desired gas components in the expiration gas and cause of specific illnesses, values of the relationship are stored in the apparatus of the embodiment of the present invention. And, the apparatus is configured to issue an alert, when a user measures the expiration gas using the apparatus, if the desired gas component concentration is greater than the stored value. Accordingly, the user can know cause of specific illness conveniently and easily.

Modified Example 5

In the modified example 4, it is also possible to provide a server or the like, of a medical organization, on a network with all or a part of functions of the data recording unit and the data analyzing unit in configurations of the embodiment of the present invention. According to this configuration, it becomes possible to transfer data of the sensor sensitivity according to the embodiment of the present invention to the server or the like, of the medical organization, on a network in realtime, as necessary, and to cause the server to record the data or to analyze the data. Based on the result, it becomes possible to get expiration diagnosis by a specialist such as a doctor of the medical organization. Also, as necessary, the result can be reported to (or displayed on) the mobile phone, so that it becomes possible to construct a bi-directional health management system, a health advice system, a diet management system, a diet effect checking system, an expiration diagnosis system or the like.

The present invention is not limited to the specifically disclosed embodiments, and variations and modifications may be made within the scope of the claims.

The present international application claims priority based on Japanese patent application No. 2011-119513, filed in the JPO on May 27, 2011, and the entire contents of the Japanese patent application No. 2011-119513 are incorporated herein by reference.

DESCRIPTION OF REFERENCE SIGNS 1 gas sensor A
2 gas sensor B
3 sensor unit
4 control unit
5 data recording unit
6 data analyzing unit
7 biological gas
8 gas component A
9 gas component B
10 gas component C
11 gas sensor A
12 gas sensor B 13 sensor unit
14 control unit
15 data recording unit
16 data analyzing unit
17 sensor block
19 expiration gas blowing opening
20 pump
21 pseudo expiration gas
22 acetone
23 hydrogen
24 ethanol

The invention claimed is:

1. A biological gas detection apparatus comprising:
a sensor unit including plural types of gas sensors;
a control unit of the sensor unit;
a data recording unit; and
a data analyzing unit, wherein
the data recording unit includes a database on properties of sensitivities of the gas sensors for a single body of a desired gas component, a single body of an interference gas component, and a mixed gas of these that are included in the biological gas, and
the data analyzing unit calculates concentration of the desired gas component based on sensitivities of the as sensors which are output when performing detection of the biological gas and the properties of sensitivities of the gas sensors included in the database, and
if a sum of sensitivity of the gas sensors is greater than a predetermined first threshold, the biological gas detection apparatus determines that the concentration of the desired gas component is very low as though the desired gas component can be regarded as being absent, or that there is a problem during measurement.

2. The biological gas detection apparatus as claimed in claim 1, wherein
two types of the gas sensors are provided, in which a first gas sensor is a semiconductor type gas sensor having relatively high detection capability for the desired gas component, a second gas sensor is a semiconductor type gas sensor that has detection capability at least for the interference gas component and that has sensing gas properties different from the first gas sensor.

3. The biological gas detection apparatus as claimed in claim 1, wherein
the desired gas component is acetone.

4. The biological gas detection apparatus as claimed in claim 1, wherein
main gas components of the interference gas component are ethanol and hydrogen, and at least one type of these is an interference gas for the desired gas component.

5. The biological gas detection apparatus as claimed in claim 1, further comprising:
a biological gas introduction unit configured to introduce the biological gas into the sensor unit.

6. A biological gas detection apparatus comprising:
a sensor unit including plural types of gas sensors;
a control unit of the sensor unit;
a data recording unit; and
a data analyzing unit, wherein
the data recording unit includes a database on properties of sensitivities of the gas sensors for a single body of a desired gas component, a single body of an interference gas component, and a mixed gas of these that are included in the biological gas, and
the data analyzing unit calculates concentration of the desired gas component based on sensitivities of the gas sensors which are output when performing detection of the biological gas and the properties of sensitivities of the gas sensors included in the database, and
if sensitivity of a second gas sensor is greater than a predetermined threshold, the biological gas detection apparatus calculates concentration of the desired gas component based on a sensitivity of a first gas sensor output when performing detection of the biological gas and the properties of sensitivities of the gas sensors included in the database.

7. A biological gas detection apparatus comprising:
a sensor unit including plural types of gas sensors;
a control unit of the sensor unit;
a data recording unit; and
a data analyzing unit, wherein
the data recording unit includes a database on properties of sensitivities of the gas sensors for a single body of a desired gas component, a single body of an interference gas component, and a mixed gas of these that are included in the biological gas, and
the data analyzing unit calculates concentration of the desired gas component based on sensitivities of the gas sensors which are output when performing detection of the biological gas and the properties of sensitivities of the gas sensors included in the database, and
if sensitivity of a second gas sensor is equal to or less than a predetermined threshold and a sensitivity ratio of a first gas sensor and the second gas sensor is greater than a predetermined second threshold, the biological gas detection apparatus calculates concentration of the desired gas component based on a sensitivity of the first gas sensor output when performing detection of the biological gas and the properties of sensitivities of the gas sensors included in the database.

8. A biological gas detection apparatus comprising:
a sensor unit including plural types of gas sensors;
a control unit of the sensor unit;
a data recording unit; and
a data analyzing unit, wherein
the data recording unit includes a database on properties of sensitivities of the gas sensors for a single body of a desired gas component, a single body of an interference gas component, and a mixed gas of these that are included in the biological gas, and
the data analyzing unit calculates concentration of the desired gas component based on sensitivities of the gas sensors which are output when performing detection of the biological gas and the properties of sensitivities of the gas sensors included in the database, and
if sensitivity of a second gas sensor is equal to or less than a predetermined threshold and a sensitivity ratio of a first gas sensor and the second gas sensor is equal to or less than a predetermined second threshold, the biological gas detection apparatus calculates concentration of the interference gas component based on a sensitivity of the second gas sensor output when performing detection of the biological gas and the properties of sensitivities of the gas sensors included in the database, and calculates concentration of the desired gas component based on the interference gas component concentration, a sensitivity of the first gas sensor output when performing detection of the biological gas and the properties of sensitivities of the gas sensors included in the database.

9. A biological gas detection apparatus comprising:
a sensor unit including plural types of gas sensors;
a control unit of the sensor unit;
a data recording unit; and
a data analyzing unit, wherein the data recording unit includes a database on properties of sensitivities of the gas sensors for a single body of a desired gas component, a single body of an interference gas component, and a mixed gas of these that are included in the biological gas, and the data analyzing unit calculates concentration of the desired gas component based on sensitivities of the gas sensors which are output when performing detection of the biological gas and the properties of sensitivities of the gas sensors included in the database, and if sensitivity of a second gas sensor is greater than a predetermined threshold, the biological gas detection apparatus calculates concentration of the desired gas component based on sensitivity of a first gas sensor output when performing detection of the biological gas and the properties of sensitivities of the gas sensors included in the database.

10. A biological gas detection apparatus comprising:
a sensor unit including plural types of gas sensors;
a control unit of the sensor unit;
a data recording unit; and
a data analyzing unit, wherein
the data recording unit includes a database on properties of sensitivities of the gas sensors for a single body of a desired gas component, a single body of an interference gas component, and a mixed gas of these that are included in the biological gas, and the data analyzing unit calculates concentration of the desired gas component based on sensitivities of the gas sensors which are output when performing detection of the biological gas and the properties of sensitivities of the gas sensors included in the database, and if sensitivity of a second gas sensor is equal to or less than a predetermined threshold and sensitivity of a first gas sensor is equal to or less than a predetermined second threshold, the biological gas detection apparatus calculates concentration of the desired gas component based on sensitivity of the first gas sensor output when performing detection of the biological gas and the properties of sensitivities of the gas sensors included in the database.

11. A biological gas detection apparatus comprising:
a sensor unit including plural types of gas sensors;
a control unit of the sensor unit;
a data recording unit; and
a data analyzing unit, wherein
the data recording unit includes a database on properties of sensitivities of the gas sensors for a single body of a desired gas component, a single body of an interference gas component, and a mixed gas of these that are included in the biological gas, and the data analyzing unit calculates concentration of the desired gas component based on sensitivities of the gas sensors which are output when performing detection of the biological gas and the properties of sensitivities of the gas sensors included in the database, and if sensitivity of a second gas sensor is equal to or less than a predetermined threshold and sensitivity of a first gas sensor is greater than a predetermined second threshold, the biological gas detection apparatus calculates concentration of the interference gas component based on a sensitivity of the second gas sensor output when performing detection of the biological gas and the properties of sensitivities of the gas sensors included in the database, and calculates concentration of the desired gas component based on the interference gas component concentration, a sensitivity of the first gas sensor output when performing detection of the biological gas and the properties of sensitivities of the gas sensors included in the database, and calculates concentration of the desired gas component based on the interference gas component concentration, a sensitivity of the first gas sensor output when performing detection of the biological gas and the properties of sensitivities of the gas sensors included in the database.

12. A biological gas detection method performed by a biological gas detection apparatus configured to detect and calculate concentration of a desired gas component in a biological gas including an interference gas without separating the component, the method comprising:

calculating concentration of the desired gas component based on sensitivities of plural types of gas sensors which are output when performing detection of the biological gas and properties of sensitivities of the gas sensors included in a database, wherein the database includes properties of sensitivities of the gas sensors for a single body of a desired gas component, a single body of an interference gas component, and a mixed gas of these that are included in the biological gas, at least two types of the gas sensors are provided, in which a first gas sensor is a semiconductor type gas sensor having relatively high detection capability for the desired gas component, and a second gas sensor is a semiconductor type gas sensor that has detection capability at least for the interference gas component and that has sensing gas properties different from the first gas sensor, the method comprises:

obtaining, by using the first and second sensors, at least
(i) relationship of sensitivity of the first gas sensor with respect to concentration of a single body of the desired gas component,
(ii) relationship of sensitivity of the first gas sensor with respect to concentration of a mixed gas when a predetermined amount of the interference gas component is added to the desired gas component, and
(iii) relationship of sensitivity of the second gas sensor with respect to concentration of a single body of the interference gas component, so as to form a database of sensitivity properties of each sensor, obtaining sensitivity of each of the first and second gas sensors by measuring the biological gas by using the first and second gas sensors;

if a sum of sensitivity of the first gas sensor and sensitivity of the second gas sensor is greater than a predetermined first threshold, determining that the concentration of the desired gas component is very low as though the desired gas component can be regarded as being absent, or that there is a problem during measurement;

if sensitivity of the second gas sensor is greater than a predetermined second threshold, calculating concentration of the desired gas component based on a sensitivity of the first gas sensor output when performing detection of the biological gas and the properties of sensitivities of the gas sensors included in the database;

if sensitivity of the second gas sensor is equal to or less than the predetermined second threshold and a sensitivity ratio of the first gas sensor and the second gas sensor is greater than a predetermined third threshold, calculating concentration of the desired gas component based on sensitivity of the first gas sensor output when performing detection of the biological gas and the properties of sensitivities of the gas sensors included in the database, and if sensitivity of the second gas sensor is equal to or less than the predetermined second threshold and a sensitivity ratio of the first gas sensor and the second gas sensor is equal to or less than the predetermined third threshold, calculating concentration of the interference gas component based on a sensitivity of the second gas sensor output when performing detection of the biological gas and the properties of sensitivities of the gas sensors included in the database, and calculating concentration of the desired gas component based on the interference gas component concentration, a sensitivity of the first gas sensor output when performing detection of the biological gas and the properties of sensitivities of the gas sensors included in the database.

13. A biological gas detection method performed by a biological gas detection apparatus configured to detect and calculate concentration of a desired gas component in a biological gas including an interference gas without separating the component, the method comprising:

calculating concentration of the desired gas component based on sensitivities of plural types of gas sensors which are output when performing detection of the biological gas and properties of sensitivities of the gas sensors included in a database, wherein the database includes properties of sensitivities of the gas sensors for a single body of a desired gas component, a single body of an interference gas component, and a mixed gas of these that are included in the biological gas, at least two types of the gas sensors are provided, in which a first gas sensor is a semiconductor type gas sensor having relatively high detection capability for the desired gas component, and a second gas sensor is a semiconductor type gas sensor that has detection capability at least for the interference gas component and that has sensing gas properties different from the first gas sensor, the method comprises:

obtaining, by using the first and second sensors, at least (i) relationship of sensitivity of the first gas sensor with respect to concentration of a single body of the desired gas component, (ii) relationship of sensitivity of the first gas sensor with respect to concentration of a mixed gas when a predetermined amount of the interference gas component is added to the desired gas component, and (iii) relationship of sensitivity of the second gas sensor with respect to concentration of a single body of the interference gas component, so as to form a database of sensitivity properties of each sensor, obtaining sensitivity of each of the first and second gas sensors by measuring the biological gas by using the first and second gas sensors;

if sensitivity of the second gas sensor is greater than a predetermined first threshold, calculating concentration of the desired gas component based on a sensitivity of the first gas sensor output when performing detection of the biological gas and the properties of sensitivities of the gas sensors included in the database;

if sensitivity of the second gas sensor is equal to or less than the predetermined first threshold and sensitivity of the first gas sensor is equal to or less than a predetermined second threshold, calculating concentration of the desired gas component based on a sensitivity of the first gas sensor output when performing detection of the biological gas and the properties of sensitivities of the gas sensors included in the database; and if sensitivity of the second gas sensor is equal to or less than the predetermined first threshold and sensitivity of the first gas sensor is greater than the predetermined second threshold, calculating concentration of the interference gas component based on a sensitivity of the second gas sensor output when performing detection of the biological gas and the properties of sensitivities of the gas sensors included in the database, and calculating concentration of the desired gas component based on the interference gas component concentration, a sensitivity of the first gas sensor output when performing detection of the biological gas and the properties of sensitivities of the gas sensors included in the database.

* * * * *